United States Patent [19]

Rosencwaig

[11] Patent Number: 5,657,754

[45] Date of Patent: Aug. 19, 1997

[54] APPARATUS FOR NON-INVASIVE ANALYSES OF BIOLOGICAL COMPOUNDS

[76] Inventor: Allan Rosencwaig, 3304 Deer Hollow Dr., Danville, Calif. 94506

[21] Appl. No.: 500,120

[22] Filed: Jul. 10, 1995

[51] Int. Cl.$^6$ ........................................... A61B 5/00
[52] U.S. Cl. ........................ 128/633; 128/664; 128/665
[58] Field of Search ................................. 128/633, 664, 128/665

[56] References Cited

U.S. PATENT DOCUMENTS

| | | | |
|---|---|---|---|
| 3,948,345 | 4/1976 | Rosencwaig | 181/5 |
| 4,059,010 | 11/1977 | Sach | 73/596 |
| 4,273,421 | 6/1981 | Gurtler | 350/353 |
| 4,495,949 | 1/1985 | Stoller | 128/664 |
| 4,513,384 | 4/1985 | Rosencwaig | 364/563 |
| 4,521,118 | 6/1985 | Rosencwaig | 374/5 |
| 4,545,387 | 10/1985 | Balique | 128/664 X |
| 4,579,463 | 4/1986 | Rosencwaig et al. | 374/57 |
| 4,600,011 | 7/1986 | Watmough | 128/664 |
| 4,632,561 | 12/1986 | Rosencwaig et al. | 356/432 |
| 4,634,290 | 1/1987 | Rosencwaig et al. | 374/5 |
| 4,636,088 | 1/1987 | Rosencwaig et al. | 374/5 |
| 4,768,516 | 9/1988 | Stoddart et al. | 128/664 X |
| 4,819,752 | 4/1989 | Zelin | 128/664 X |
| 4,829,184 | 5/1989 | Nelson et al. | 128/664 X |
| 4,836,203 | 6/1989 | Müller et al. | 128/664 X |
| 5,042,952 | 8/1991 | Opsal et al. | 356/432 |
| 5,348,002 | 9/1994 | Caro | 128/664 X |
| 5,408,327 | 4/1995 | Geiler et al. | 356/432 |
| 5,551,422 | 9/1996 | Simonsen et al. | 128/664 X |
| 5,553,616 | 9/1996 | Ham et al. | 128/633 |

FOREIGN PATENT DOCUMENTS

| | | | |
|---|---|---|---|
| 62-34040 | 2/1987 | Japan | G01N 21/88 |
| 930286307 | 5/1995 | Japan . | |
| WO91/15990 | 10/1991 | WIPO . | |
| WO92/10131 | 6/1992 | WIPO . | |
| WO93/22649 | 11/1993 | WIPO . | |

OTHER PUBLICATIONS

International Search Report, dated Nov. 11, 1996, International Patent Application No. PCT/US96/10877, with an International Filing Date of Jun. 25, 1996, 4 pages in length.
*Photoacoustics and Photoacoustic Spectroscopy*, Chapt. 17 ("Studies in Biology"), Chapt. 18 (Studies in Medicine) and Chapt. 21 (Depth-Profiling and Thickness Measurements), by Allan Rosencwaig, vol. 57 in Chemical Analysis, 1980, pp. 207-218, 219-244 and 270-284.
J. Opsal & A. Rosencwaig, "Thermal and plasma wave depth profiling in silicon," *Appl. Phys. Lett.*, vol. 47, No. 5, Sep. 1, 1985, pp. 498-500.

(List continued on next page.)

*Primary Examiner*—Angela D. Sykes
*Assistant Examiner*—Stephen Huang
*Attorney, Agent, or Firm*—Limbach & Limbach L.L.P.

[57] ABSTRACT

An apparatus for the non-invasive analysis of non-homogeneous samples is disclosed. The apparatus is particularly suited for analyzing biological samples having different constituents. An intensity modulated light beam is used to preferentially heat a selected constituent in the sample. This periodic heating will create thermal waves in the sample. A probe beam is directed to interact with the sample in the region which has been periodically heated. A phase synchronous detector is used to monitor the periodic changes in the probe beam caused by the thermal waves in the sample. In the preferred embodiment for monitoring blood glucose levels, the wavelength of the modulated light beam is selected to be absorbed in the hemoglobin of the red blood cells. The modulation frequency of the light beam is selected to set the thermal diffusion length of the thermal waves to permit interaction with the glucose molecules in the blood plasma. In addition, the phase synchronous detector is configured to monitor signals which occur ninety degrees out of phase with the modulation of the heating beam. In this manner, the output from the system can be most accurately targeted to the constituent of interest.

78 Claims, 4 Drawing Sheets

OTHER PUBLICATIONS

A. Rosencwaig, "Depth Profiling of Integrated Circuits with Thermal Wave Electron Microscopy," *Electronics Letters*, vol. 16, No. 24, Nov. 20, 1980, 2 pages in length.

E. Brandis & A. Rosencwaig, "Thermal–wave microscopy with electron beams," *Appl. Phys. Lett.*, vol. 37, No. 1, Jul. 1, 1980, pp. 98–100.

G. Busse & A. Rosencwaig, "Subsurface imaging with photoacoustics," *Appl. Phys. Lett.*, vol. 36, No. 10, May 15, 1980, pp. 815–816.

A. Rosencwaig & G. Busse, "High–resolution photoacoustic thermal–wave microscopy," *Appl. Phys. Lett.*, vol. 36, No. 9, May 1, 1990, pp. 725–727.

APPARATUS FOR NON-INVASIVE ANALYSES OF BIOLOGICAL COMPOUNDS

TECHNICAL FIELD

The subject invention relates to a device for the non-invasive analyses of particular constituents in a non-homogeneous sample. The apparatus can be used for the in-vivo monitoring of glucose levels in the blood stream of a patient.

BACKGROUND OF THE INVENTION

There has been significant interest in developing devices which permit the non-invasive monitoring of constituents in the blood and tissues of the body. Some success has been achieved in designing devices which measure the oxygen content in the blood. The devices are known as oxymeters.

Oxymeters determine the level of oxygen in the blood by measuring the amount of light absorbed in the tissue. In operation, a probe beam is generated having a wavelength in the 400 to 600 nanometer range. The probe beam is directed through the tissue into the blood stream. The portion of the blood stream carrying oxygen (oxyhemoglobin) has a high level of absorption in this wavelength range. Non-oxygenated hemoglobin and other human tissue are much more transmissive at these wavelengths. Accordingly, by measuring the level of absorption which occurs when the probe beam light passes through the tissue, the level of oxygen in the blood can be determined.

This approach for the non-invasive analysis of oxygen content in the blood has been relatively successful due to a few factors. First, there is a considerable amount of blood present in the human body (ten percent) and the red blood cells, which contain the hemoglobin, account for forty-five percent of the total volume of the blood. In addition, and as noted above, certain light wavelengths exist which are highly absorbed in oxygenated blood and which have much lower absorption levels in the other constituents of the body.

Attempts to use optical absorption schemes to analyze other constituents in the body have been much less successful because the conditions are less favorable. For example, many other constituents of interest are present in much lower concentrations in the body. Moreover, even though the constituents of interest will have certain specific absorption bands, these absorption bands are typically shared with other constituents in the body. Therefore, isolation and measurement of particular constituents by optical absorption has not been possible.

One constituent in the body for which there is great interest in developing non-invasive monitoring techniques is glucose, since monitoring glucose levels can significantly aid in the treatment of diabetes. It is now well established that a principal method of preventing some of the more serious effects of diabetes is to regularly monitor the glucose level in the blood stream and then maintain that level within a normal range. At the present time, the most common method for monitoring glucose levels requires obtaining a small blood sample. The blood sample is then subjected to a chemical reaction wherein the glucose is oxidized to form gluconic acid, hydrogen peroxide and a hydronium ion. This reaction can be monitored using dry chemical strips either spectrophotometrically or electrochemically.

The use of the glucose strip method has become quite common. Unfortunately, this approach is painful, messy, complex, expensive and prone to error. In addition, since the skin must be pierced and blood drawn, issues regarding the spread of life threatening infections arise.

Efforts are underway to provide alternatives to the blood-glucose strip method. At the present time, attempts are being made to monitor glucose levels in saliva, sweat, subcutaneous tissue and the eye. However, glucose concentrations, particularly in the saliva and sweat, lag in time behind the actual concentrations in the blood and therefore do not give an accurate picture of current glucose levels in the blood.

To avoid these problems, efforts have been made to measure blood glucose in a non-invasive manner using optical techniques similar to those used in measuring oxygen levels in the blood. One method relies upon shining near infrared light through a finger or earlobe. Unfortunately, while the glucose molecule absorbs in this wavelength region, other, more highly concentrated constituents in the body (such as water and proteins) absorb in this wavelength region as well. Thus, the absorption caused by glucose is minimal compared to the total absorption of other constituents.

Even with this minimal absorption, some positive results can be achieved by applying various forms of statistical analyses to the measurements. More specifically, by collecting data and comparing it to a calibration model, some initial success has been achieved. However, to date, various factors which tend to reduce the accuracy of the results have not been fully resolved. These factors include tissue temperature, endogenous metabolites, hemoglobin concentration, repeatability of the placement of the tested region (finger, earlobe) in the testing device and subject to subject variability.

Another technique for the non-invasive monitoring of glucose is based on the optical activity of the molecule. Glucose, like many other carbohydrates and monosaccharides is optically active. When polarized light is passed through a mixture including an optically active constituent, the axis of polarization of the light will be rotated by an amount proportional to the concentration of the optically active constituent. For typical glucose levels in the blood (approximately 100 mg/dL), the optical rotation of light will be only 5 to 9 millidegrees per centimeter path length.

Prior art polarimeters are capable of measuring optical rotation at this low level. However, the various elements of the body, including tissue, blood etc. scatter, absorb and depolarize light, such that the polarization rotation induced by the glucose will be masked. To minimize these problems, efforts have been made to monitor the optical activity of glucose by measuring the effect in the eye where scattering and absorption is minimized.

These latter efforts have provided some promising results. However, problems with scattering and absorption still exist. Moreover, the eye exhibits birefringence which also interferes with the measurement. Finally, it is unknown how comfortable patients will be shining lights into their eyes to measure glucose levels.

Accordingly, there is still a strong need to develop an accurate, non-invasive technique for monitoring glucose levels in the blood.

The invention described herein addresses this need through the use of a thermal wave excitation and detection system. The concept and approaches for evaluating samples using a thermal wave type analysis are well established today. Commercial thermal wave detection systems are employed primarily in the semiconductor fabrication field where the devices are used to monitor ion implant dosage, defects and other features. Examples of such systems can be found in the following U.S. Pat. Nos. 4,521,118; 4,522,510; 4,636,088; 4,579,463; 4,634,290 and 4,632,561.

In general, thermal wave detection systems include a means for creating a periodic heating in the sample. In the case of the equipment discussed above, the preferred heat source is an intensity modulated laser beam which can be tightly focused to the micron range important for semiconductor analysis. The periodic heat source functions to generate periodic thermal waves which propagate outwardly interacting with various features in the sample. These thermal waves will function to periodically vary a number of different physical and optical parameters of the sample such as reflectivity, transmission, absorption, scattering and local deformation of the sample surface.

The variations of these different parameters can be monitored using a number of different techniques. In the systems discussed above, the optical parameters are investigated using a probe beam of radiation which is also focused onto the sample. Periodic changes in the probe beam, such as reflected power, transmitted power or scattering, are monitored using a phase synchronous detection system. These periodic changes can provide valuable information about the surface and subsurface characteristics of the sample.

In the past, thermal wave techniques also have been used experimentally to analyze biological samples. These experiments have been primarily limited to photoacoustic spectroscopy experiments wherein the sample is heated with a modulated optical beam and the periodic absorption of this probe beam as a function of wavelength is measured. For a more complete discussion, see *Photoacoustics and Photacoustic Spectroscopy*, Allan Rosenscwaig, Wiley Interscience, 1980.

The prior investigations of both semiconductors and biological material relate to samples where it is relatively straightforward to target the constituent of interest. For example, when investigating ion dopant levels in semiconductors, the sample is treated as a uniform absorber of the pump beam and probe beams. The output signal is a function of a fairly homogeneous local region of the sample. In contrast, and as noted above, the blood stream can include a number of different constituents which inhibits the analysis of specific constituents of interest.

Accordingly, it is an object of the subject invention to provide an improved thermal wave generation and detection system which is particularly suited for investigating characteristics of non-homogeneous samples.

It is a further object of the subject invention to provide a system which can preferentially analyze selected constituents of a non-homogeneous sample.

It is another object of the subject invention to provide a system for analyzing particular constituents in the blood stream of a mammal.

It is still a further object of the subject invention to provide a system for the non-invasive monitoring of the glucose levels in the blood stream of a mammal.

It is still another object of the subject invention to provide a thermal wave detection system which provides spatial discrimination permitting analysis of selected constituents in a non-homogeneous sample

SUMMARY OF THE INVENTION

In accordance with these and other objects, the subject invention provides for a method and apparatus for analyzing the properties of a non-homogeneous sample, such as blood, which includes two or more constituents. The apparatus includes a means for periodically heating one of the constituents of the sample in a manner to create thermal waves. In one preferred embodiment, the heating means is defined by an intensity modulated light beam which is directed through the tissue in a relatively transparent blood carrying region of the body such as a finger or ear lobe.

The effects of the thermal waves generated in the sample on the constituent of interest are then monitored. These effects can be monitored optically in a known manner. For example, a probe beam can be used to measure periodic changes in transmission, absorption, reflection or scattering. Other detection schemes which rely on acoustics (ultrasound), microwaves or even magnetic resonance imaging (MRI), could be used. The monitoring approach will include a phase synchronous detector for measuring changes which occur at a frequency related to the periodicity of the heating means. As described in the references cited above, monitoring the periodic response in a phase synchronous fashion can greatly improve sensitivity.

In order to target the measurement to the constituent of interest and provide the necessary spatial discrimination, a few distinct parameters of the system should be carefully selected. First, the periodic heating source can be selected to preferentially heat one of the constituents in the sample. When the heating source is an intensity modulated light beam, the wavelength of light selected should be preferentially absorbed in the selected constituent. Similarly, if the detection system relies upon the measurement of the modulated transmission of a probe light beam, the wavelength of the probe should be preferentially absorbed in the constituent to be analyzed.

In accordance with the subject invention, the modulation frequency of the heating source should also be carefully controlled to maximize the signal from the target constituent. More specifically, thermal waves will be created in the constituent which absorbs the heating from the heat source. These thermal waves will then propagate outwardly in a spherical wavefront from the heated constituents. Thermal waves are inherently critically damped and do not travel very far. However, the length of travel (or thermal diffusion length $\mu$) is a direct function of the modulation frequency of the heating source. If the target constituent and the heated constituent are the same, then the heating frequency should be selected to minimize the thermal diffusion length so that any heating effects will be confined to the heated constituent. If the target constituent is different from the heated constituent, then the heating frequency should be selected so that the thermal waves propagate a sufficient distance to reach and interact with the target.

In still another aspect of the subject invention, the phase discrimination of the detection system should also be controlled to maximize the signal strength from the target constituent. More specifically, the approach used in most prior art thermal wave analyses was to measure signals which are in phase with the thermal wave signals. These are the signals which are at their strongest at the center of the locations which are being periodically heated. A thermal wave signal also exists which is ninety degrees out of phase ($\phi=\pi/2$) from the "in-phase" (or $\phi$=zero) signal. The $\pi/2$ signal is typically weaker than the in-phase signal. However, in the case where the target constituent is not the same as the constituent which has been heated, the frequency of the heating source can be selected so that the locus of the $\pi/2$ signal will coincide with the location of the target constituent rather than the heated constituent. By measuring the $\pi/2$ signal, information about the target constituent can be more readily evaluated.

It should be noted that the prior art does disclose the concept of varying the frequency of the modulated heat source in order to vary the diffusion length of the thermal waves. (See, for example, U.S. Pat. No. 4,513,384). In addition, there has also been some general discussion of the concept of adjusting the phase relationship between the lock-in detector and the pump modulator in thermal wave systems. (See, for example, "Depth Profiling of Integrated Circuits with Thermal Wave Electron Microscopy," Rosencwaig, Electronics Letters, Vol 16, No. 24, Nov. 20, 1980, page 928–930.) However, these disclosures were in the context of providing depth profiling of the sample, rather than attempting to isolate and enhance the measurement of specific constituents in a non-homogeneous sample. In addition, these depth profiling studies did not disclose the concepts of preferentially heating selected first constituents in the sample; selecting the modulation frequency of the heating source so that the thermal waves will interact with selected second constituents spaced away from the first constituents and then monitoring the $\pi/2$ phase signal to maximize detection of information related to the second constituents.

Further objects and advantages of the subject invention will become apparent from the following detailed discussion taken in conjunction with the drawings in which:

DETAILED DESCRIPTION OF THE PREFERRED EMBODIMENTS

Figure 1:
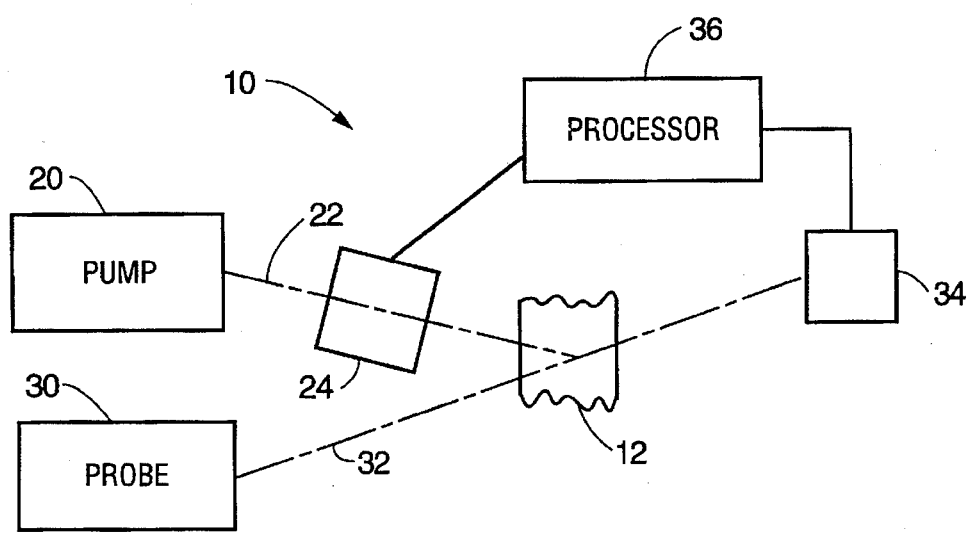
FIG. 1 is a schematic diagram of a thermal wave detection system formed in accordance with the subject invention.

FIG. 1 illustrates a basic lay-out of a system 10 for generating and detecting thermal waves in a sample 12. The system 10 includes a means for periodically heating the sample. In this embodiment, the means includes a pump source 20 generating a beam of light 22. The beam of light 22 is passed through a modulator 24 for intensity modulating the beam at a predetermined frequency $\omega$. The pump beam 22 is directed into the sample in a manner so that certain constituents therein are periodically heated.

The subject device further includes a means for monitoring the periodic effects of the thermal waves on the sample and generating an output signal in response thereto. In this embodiment, the monitoring means includes a probe source 30 for generating a beam of light 32. The probe beam 32 is directed through the sample and strikes a photodetector 34. The output of the photodetector is fed to a processor 36 which also receives an input from the modulator 24. The processor 36 functions to extract the portion of the photodetector signal which is phase synchronous with the periodic heating in the sample. In this sense, the detector and processor function together to isolate a phase synchronous signal and generate an output representative of the thermal wave interaction with the sample. The processor can also be programmed to analyze this phase synchronous output to determine properties of the sample. Thermal wave detection systems operating in a manner similar to that described above (except with reflected rather than transmitted light) have been successfully developed and sold for measuring dopant concentrations in semiconductor wafers.

The basic thermal wave detection scheme can be enhanced in order to analyze samples having multiple constituents with overlapping responses. In accordance with the subject invention, an approach is used which permits spatial discrimination of various constituents in the sample.

The subject approach is designed to address a typical non-homogeneous sample of the type associated with biological compounds. A one-dimensional model of such a system is shown in FIG. 2. This model can be useful in considering both a solid system such as human tissue as well as the constituents in a flowing liquid such as the blood stream. In either case, the spacings illustrated can be considered average spacings between constituents which are statistically representative of the actual distribution in the sample.

In this single axis representation, elements X, Y and Z are dispersed throughout the sample. If a non-discriminatory heat source were to be used, thermal waves would be generated uniformly across the sample and no spatial discrimination would be possible.

In accordance with the subject invention, a periodic heat source is chosen which can selectively heat a particular constituent. In this example, a heat source is selected which is preferentially absorbed in constituent X. The periodic heating of constituent X will cause spherical thermal waves 40 to be generated emanating from each of the constituent X sites.

Figure 2A:
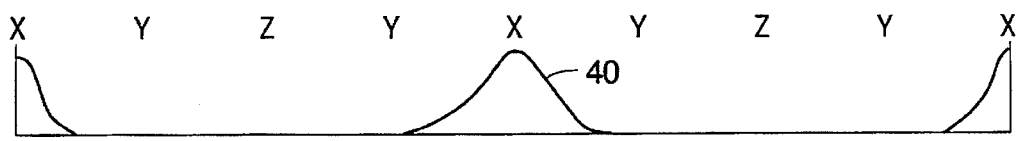
FIGS. 2a, 2b and 2c illustrate how variations in the thermal diffusion length can be used to target selected constituents in a sample.

In FIG. 2a, the thermal waves 40 are shown with a relatively short diffusion length. This short diffusion length corresponds to a higher modulation frequency of the heating source. As can be seen, the thermal waves are concentrated in the region of constituent X and interact only slightly with the adjacent constituents Y. Accordingly, if a standard, phase-locked thermal wave signal is measured, it will necessarily correspond primarily to the interaction of the thermal waves with constituent X.

The subject system can also be configured to investigate a target constituent which is different and spatially separated from the constituent that has been periodically heated. This approach is shown in FIGS. 2b and 2c.

Figure 2B:
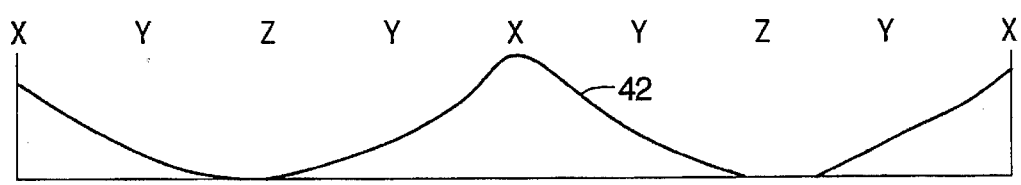
Figure 2C:
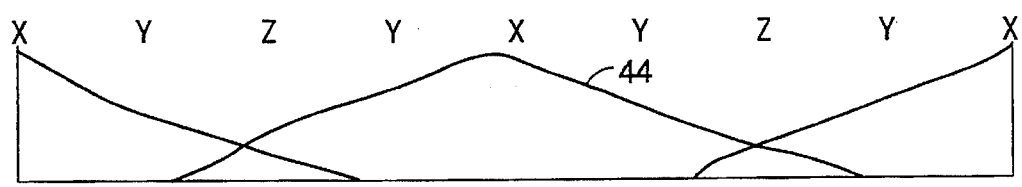

In FIG. 2b, the diffusion length of the thermal wave 42 has been increased. This can be accomplished by lowering the modulation frequency of the heating source. In this case, the thermal wave will interact strongly with both constituents X and Y, and only slightly with constituent Z. In FIG. 2c, the diffusion length of the thermal wave 44 has been increased still further, also by lowering the modulation frequency of the heating source. In this situation, the thermal waves 44 will interact with all three constituents, X, Y and Z.

In order to extract information about a constituent which is spatially separated from the constituent which is being heated, the thermal wave signal which is ninety degrees out of phase with the periodic heating is measured. This fact can best be appreciated by recognizing that (for a one-dimensional model) the strength of the thermal wave signal is given by the following equation:

$$T_{(x)} = T_0 e^{-x/\mu} \cos[\omega t - (x/\mu)] \tag{1}$$

where x is the distance from the periodic heat source, $\mu$ is the thermal diffusion length, $\omega$ is the radial modulation frequency and t is time. The bulk of the signals which can be detected that are exactly in-phase with the periodic heat source ($\phi = \omega t =$ zero) will result primarily from the thermal wave interaction with the sample in the region coinciding with the origin of the periodic heating. On the other hand, the bulk of the signals which can be detected that are ninety degrees out of phase with the periodic heat source ($\phi = \omega t = \pi/2$) will result primarily from the thermal wave interaction with the sample roughly one thermal diffusion length away from the origin of the periodic heating.

Thus, if there was interest investigating constituent Y, the thermal diffusion length could be set as shown in FIG. 2b and the thermal wave signal should be measured at $\pi/2$ with respect to the periodic heating. By this arrangement, the thermal wave signal will be predominated by the interaction between the thermal waves and constituent Y. Similarly, if there was interest in investigating constituent Z, the thermal diffusion length could be set as shown in FIG. 2c and the $\pi/2$ signal measured. It should be understood that in the context of the specification and claims, monitoring a signal which is close to, but not exactly ninety degrees out of phase with the periodic heat source, would produce similar results.

The signal separation for different constituents can be maximized by setting the thermal diffusion length to maximize the $\pi/2$ signal with respect to the in-phase signal. This ratio is maximized when the thermal diffusion length is set to be equal to $(2/\pi)d$, where d is the spacing between the constituents X and Y. This relationship can be shown by the following $$T(d, \phi=0) = T_0 e^{-d/\mu} \cos(d/\mu) \tag{2}$$

$$T(d, \phi=\pi/2) = T_0 e^{-d/\mu} \sin(d/\mu) \tag{3}$$

$$\frac{T(d, \phi = \pi/2)}{T(d, \phi = 0)} = \tan(d/\mu) \tag{4}$$

The ratio of equation (4) is maximized when $(d/\mu) = \pi/2$.

The general formula for determining the thermal diffusion length $\mu$ in a material is as follows:

$$\mu = (2\kappa/\rho C \omega)^{1/2} \tag{5}$$

where:

$\kappa$ = thermal conductivity (calories/cm-sec-°C.)

$\rho$ = density (grams/cm$^3$)

C = specific heat (calories/gram-°C.)

$\omega$ = radial modulation frequency ($2\pi f$)

Since most biological matter is composed mainly of water, a fairly accurate approximation of the thermal diffusion length in biological matter can be derived using the thermal properties of water as follows:

$\kappa = 1.4 \times 10^{-3}$ calories/cm-sec-°C.

$\rho = 1.0$ grams/cm$^3$

C = 1.0 calories/gram-°C.

Using equation (5) above, the thermal diffusion length $\mu$ in biological tissue will be as follows for the modulation frequencies set forth below:

100 Hz $\mu \approx 21$ microns 1 kHz $\mu \approx 6.6$ microns 10 kHz $\mu \approx 2.1$ microns 100 kHz $\mu \approx 0.66$ microns 1 mHz $\mu \approx 0.2$ microns To further enhance the ability to discriminate between selected constituents, it may also be desirable to carefully select the wavelength of the probe light source. More specifically, in cases where the modulated transmission of the probe beam light is being monitored, the wavelength of the probe light source should, if possible, be selected to be preferentially absorbed in the constituent of interest. As noted above, the absorption spectra for many biological materials overlap, such that proper selection of the probe beam wavelength cannot alone provide adequate discrimination. However, as an added parameter to the selection criteria discussed above (including selection of the pump beam wavelength, modulation frequency and phase discrimination), proper selection of the probe beam wavelength can further enhance the detection system.

In order to obtain even more accurate results, it would be desirable to use more than one wavelength for the probe beam. More specifically, thermal wave data generated at a plurality of wavelengths can help reduce measurement ambiguities. Although low cost portable test devices may be limited to the use of a single probe beam wavelength, to the extent the subject invention is used for office or laboratory testing, spectroscopic capabilities would be desirable.

Figure 3:
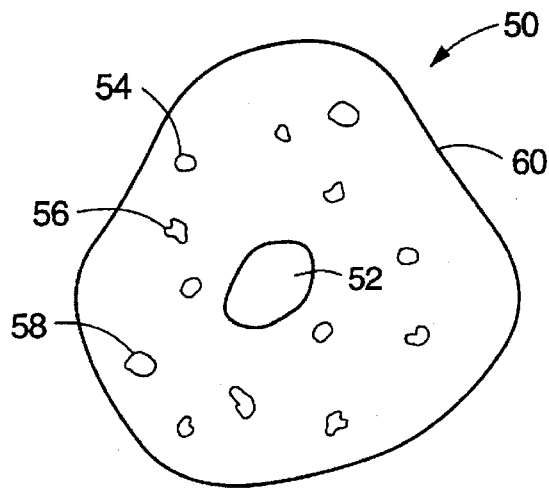
FIG. 3 is schematic representation of a tissue cell.

There are a wide variety of body structures and systems which could be analyzed using a thermal wave detection device which permits spatial discrimination. For example, the subject system could be used to monitor constituents within individual body cells. FIG. 3 is graphic representation of a typical cell 50 having a nucleus 52 and many other constituents (54, 56 and 58) within the cell membrane 60. By properly selecting the wavelengths of the pump and probe beams, the modulation frequency of the pump beam and phase discrimination of the processor, selected regions within the cell can be preferentially examined.

For example, if it were desired to investigate the protein constituents residing in the nucleus without interference from the protein constituents found in the cell fluid or cell membrane, the wavelength of the pump source would be selected to preferentially excite at least one constituent in the nucleus. The pump modulation frequency would be set relatively high (e.g. one mHz) so that the thermal diffusion length would be about 0.2 microns, short enough so that the thermal waves would not propagate much beyond the nucleus. Measurements would then be taken in phase with the excitation source ($\phi$=zero). Conversely, if it were desired to investigate the proteins outside of the nucleus, a lower modulation frequency could be used and detection would be carried out with the $\pi/2$ signal.

Figure 4:
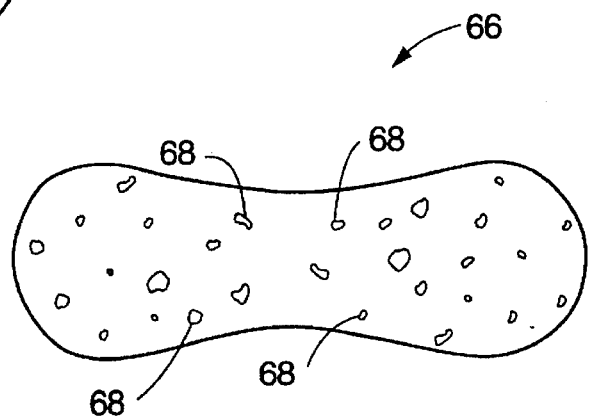
FIG. 4 is a schematic representation of a red blood cell.

The general concepts described above can be used to obtain information about specific constituents of interest. For example, the subject system could be used to monitor the oxygen level in the blood. A typical blood cell 66 is shown in FIG. 4. Unlike other cells in the body, mature blood cells do not include nuclei. Hemoglobin molecules 68 are the principle constituent in blood cells. These hemoglobin molecules are the primary carriers of oxygen for the blood and are uniformly distributed in the interior of the red blood cells. Oxygenated hemoglobin molecules absorb light in the 400 to 600 nanometer range. Accordingly, these molecules can be preferentially heated using a pump beam of that wavelength.

Assuming that the hemoglobin in the red blood cells is the constituent of interest, the pump beam will be modulated at a relatively high frequency so that the thermal waves will not propagate much beyond the walls of the red blood cells. As discussed in more detail below, red blood cells have a size in the micron range, so a modulation frequency of about 100 kHz could be selected. As noted above, a modulation frequency of 100 kHz will produce thermal waves having a diffusion length of about 0.66 microns which should effectively confine the signal to the red blood cells. The detector will be phase synchronized with the modulation frequency of the pump beam at $\phi$=zero.

If the constituents of interest are not the hemoglobin molecules of the red blood cells, but constituents outside the red blood cells, then the thermal diffusion length should be increased by lowering the modulation frequency of the pump beam. A specific example of this alternative approach is discussed below with respect to glucose monitoring.

To distinguish between the pump and probe beams, it would be desirable to use two different wavelengths. In this manner, an optical filter can be placed in front of the detector to block light from the pump beam. For this application, although the wavelengths of the pump and probe beams should be different, it would be desirable if both beams fell within absorption range for hemoglobin.

Other approaches could be used to distinguish between the pump and probe beams. For example, the beams could be polarized along different axes allowing the pump beam to be filtered from the detector with a suitable linear polarizer. It would also be possible to shorten the diffusion length of the thermal-wave and measure the $\pi/2$ signal which corresponds to a location where the contribution from the pump will be close to zero and any detected signal will be a result of the thermal wave response in the probe. Another alternative, discussed in more detail below, is to modulate both the pump and probe beams at two different frequency and detect a periodic response in the combined output beams at a sum or difference frequency.

In a further aspect of the subject invention, measurement accuracy can be enhanced by taking measurements both in phase and ninety degrees out of phase. The pump modulation frequency would be selected so that the thermal diffusion length was equal to about one-half the distance between the red blood cells. In this case, the $\phi$=zero signal will be a function of the red blood cells along with other tissue variables while the $\pi/2$ signal will primarily be a function of the other tissue variables excluding the red blood cells. The $\pi/2$ signal can now be used to normalize the $\phi$=zero signal to obtain more accurate results.

The concept of setting the thermal diffusion length to be equal to one-half the distance between red blood cells is also useful for evaluating constituents in the blood plasma. More specifically, and as noted above, most plasma constituents of interest (such as glucose) cannot be preferentially excited with a specific wavelength. In fact, the primary absorption bands of glucose are similar to the even stronger absorption bands of the more prevalent water molecule which will prevent selective excitation.

Therefore, in accordance with the subject invention, a system can be set up where the thermal waves are generated in the hemoglobin of the red blood cells using a pump beam having a wavelength in the 400 to 600 nanometer range. The modulation frequency of the pump is set so that thermal diffusion length is on the order of one-half the distance between red blood cells. In addition, the detection scheme is set up to measure the $\pi/2$ signal which will primarily correspond to the locations outside the red blood cells. In this manner, a signal from the constituents in the blood plasma can be generated.

Figure 5:
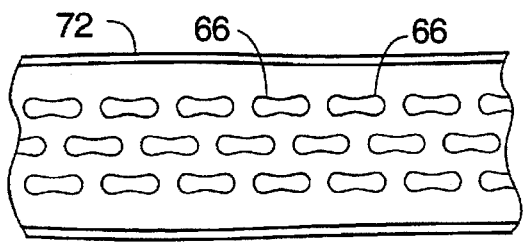
FIG. 5 is a schematic representation of red blood cells in a blood vessel.

In order to determine the proper modulation frequency, a simplified framework for the distribution of red blood cells 66 in a blood vessel 72 can be constructed in a manner shown in FIG. 5. Most red blood cells are roughly in the form of disks. In the illustrated model, the disks are lined up end to end. The average thickness of these disks is known to be about 1.9 microns. In this model, the interlayer spacing is defined as $d_1$. Since blood cells account for about forty-five percent of the blood volume, the volume of red blood cells per cubic centimeter is 0.45 cm$^3$. Therefore, on average, the spacing between the red blood cells should be $$d_1 = 1.9/0.45 = 4.22 \text{ microns} \tag{5}$$

Based on this calculation, the thermal diffusion length should be one-half of 4.22 microns or 2.11 microns. Assuming the blood consists primarily of water molecules, the modulation frequency should be on the order of 10 kHz and measurements should be taken at $\pi/2$ to target the constituents in the plasma.

All of the examples above have thus far been limited to measuring the periodic absorption of the probe beam in the sample. This approach could be used for glucose as well. However, for glucose, it also would be possible to combine the proposed thermal wave excitation technique with the technique for measuring optical activity of the glucose molecule.

As noted above, glucose is optically active and, therefore, the glucose in the plasma will function to rotate the polarization of an incoming probe beam. The amount of polarization rotation produced by a normal blood glucose concentration of 100 mg/dl is quite small (5 to 9 millidegrees per centimeter path length). Fortunately, glucose is the only constituent in the human body which will cause any measurable rotation. Unfortunately, prior art polarimeter techniques for measuring the optical activity of glucose have met with limited success. The principal problems with the prior art approaches related to low signal strength and depolarization effects of the skin.

It is believed that the thermal wave modulated response will enhance the available signal making detection easier for a number of reasons. First, using the schemes set forth above, including the proper selection of the thermal diffusion length and analyzing the $\pi/2$ signal, the response can be more accurately targeted to the glucose molecule in the plasma. Secondly, it is believed that the modulated signal will be much less affected by the depolarization effects which interfere with and weaken a typical DC signal.

Figure 6:
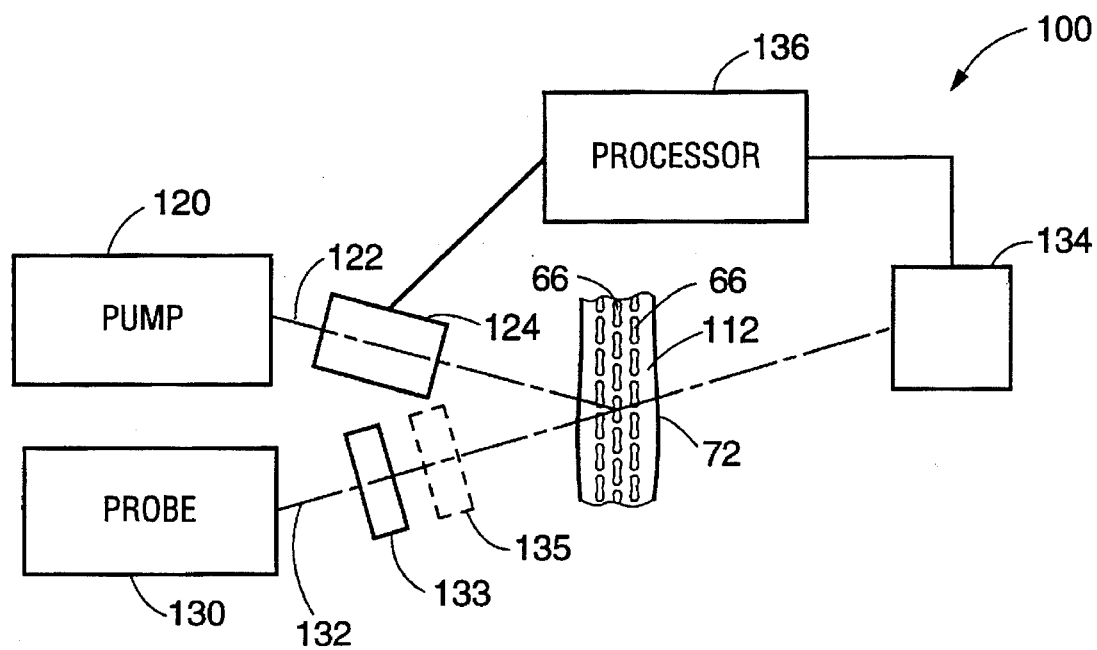
FIG. 6 is a schematic diagram of a thermal wave detection system for measuring the optical activity of a molecule.

The preferred embodiment for monitoring glucose levels based on the modulated optical activity level of the sample is illustrated in FIG. 6. In this device 100, the blood 112 can be excited with a periodic heat source 120. As presently conceived, the optimum source would consist of a light beam 122 having a wavelength selected to excite oxyhemoglobin in the red blood cells. The thermal diffusion length would be set to about 2.1 microns, or one-half the spacing between red blood cells. As noted above, this result can be achieved with a modulation frequency of about 10 kHz generated by a modulator 124.

A probe light source 130 is provided generating a probe beam 132 having a wavelength selected to maximize transmission through the tissue. Note that in this case, where modulated optical activity, rather than modulated absorption is being measured, the selection of the probe beam wavelength should minimize absorption in the tissue in order to maximize signal strength. Suitable probe beam wavelengths would fall in the visible regions of the spectrum.

The probe beam 132 is first passed through a linear polarizer 133 and then into the tissue. A detector 134 is provided which would function to measure the change in polarization state of the beam induced by the passage through the body. A variety of devices exist for measuring the changes in the polarization state of beam. Such devices, generally referred to a polarimeters, are described in greater detail in *Ellipsometry and Polarized Light*, Azzam and Bashara, North Holland, 1977. These devices usually include a "polarization analyzer" and a photodetector. The output of this detector is fed to a processor 136 along with the output of the modulator 124. The modulated optical activity of the sample can then be derived. Since the glucose is located in the plasma, the $\pi/2$ signal should be used.

In addition to rotating the plane of polarization of linearly polarized light, the optical activity of glucose in solution will also modify the characteristics of circularly polarized light. More specifically, the transmission characteristics of glucose in solution will be different for right and left-hand circularly polarized light. This property is referred to as circular dichroism. In the prior art, this property has been evaluated by alternately transmitting right and left-hand circularly polarized light through an optically active medium and measuring the transmission ratio between the polarizations. This transmission ratio can be used to determine the concentration of the glucose in the blood.

In accordance with the subject invention, glucose levels can be monitored by measuring the modulated circular dichroism in the sample. The apparatus would be similar to that shown in FIG. 6. In this case, the wavelength of the probe beam would be selected to match an absorption band in the glucose (for example, in the near-infrared region). In addition, a rotatable quarter-wave plate 135 (shown in phantom line) would be positioned in the path of the probe beam following the linear polarizer 133. The rotational position of the quarter-wave plate would be alternately changed to alternately generate right and left-hand circularly polarized light. The amount of light transmitted through the tissue would be measured by detector 134. The output of this detector is fed to the processor 136 which can calculate the ratio of the transmitted left and right-circularly polarized light.

In the prior art, circular dichroism would be monitored as an AC signal based on the rotation of the quarter-wave plate 135. In this case, the processor is connected to the modulator 124 allowing phase synchronous detection of modulated variations in the circular dichroism which occur in response to the periodic heating. Assuming the hemoglobin is being heated, the $\pi/2$ signal would be used.

Figure 7:
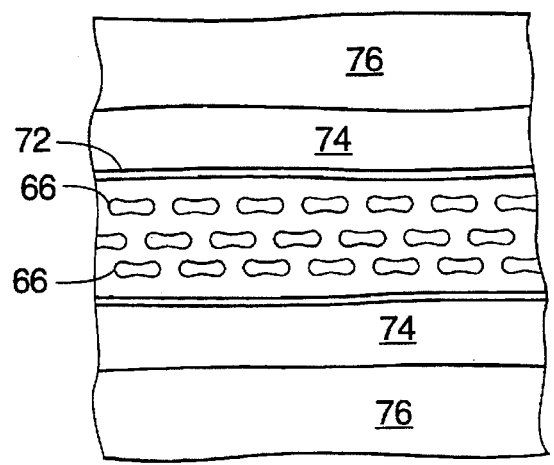
FIG. 7 is a cross-sectional illustration of a tissue sample, including a blood vessel.

The subject invention can also be utilized to investigate constituents in the tissue surrounding a blood vessel. FIG. 7 illustrates a region in the tissue having a blood vessel 72 carrying blood cells 66. A layer of a first type of tissue 74 is shown surrounding the vessel. A second layer of tissue 76 surrounds the first layer.

In accordance with the subject invention, constituents in the first layer 74 can be investigated by proper selection of the pump and probe beams as well as the phase discrimination of the detector. For this application, the pump beam can be selected to excite the hemoglobin molecules in the red blood cells in the vessel 72. The modulation frequency of the pump beam is chosen to create a thermal diffusion length that would permit the thermal waves to interact with layer 74. A probe beam wavelength will be selected which maximizes the absorption in layer 74. The processor will be arranged to monitor the $\pi/2$ signal. In this manner, information about the constituents in layer 74 can be derived.

In each of the embodiments discussed above, the detector was arranged to measure the probe beam after it has been transmitted through the sample. In the past, the thermal wave response has also been monitored using both reflection and scattering detection techniques.

Figure 8:
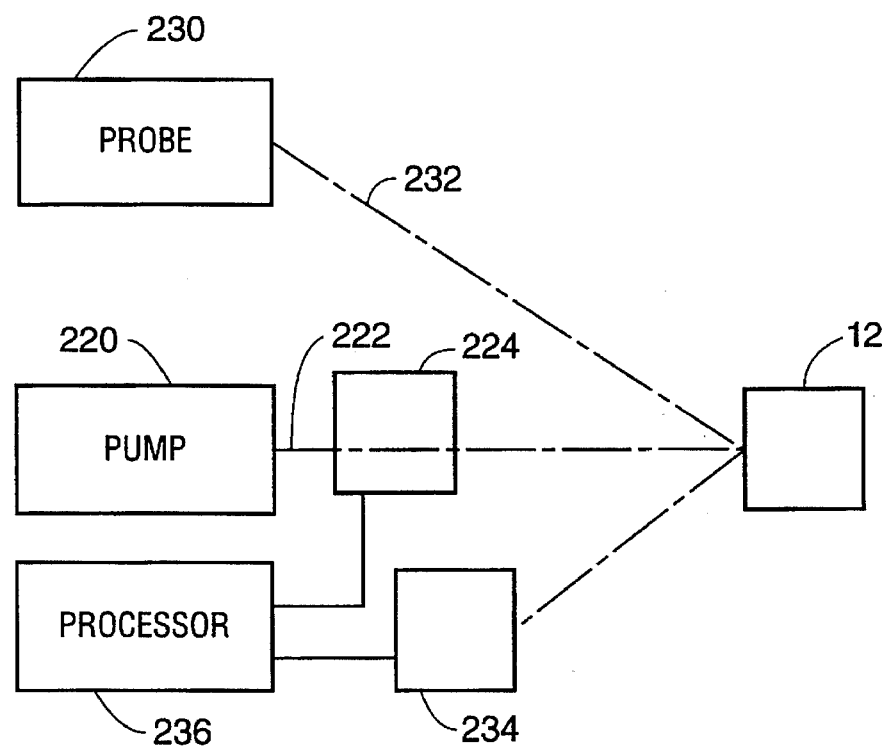
FIG. 8 is a schematic diagram of a thermal wave detection system for monitoring the modulated optical reflectance of a probe beam.

FIG. 8 is a schematic diagram of a thermal wave system for monitoring the modulated optical reflectance of a probe beam. In this example, a pump source 220 generates a pump beam 222 which is passed through a modulator 224 to periodically heat selected constituents in the sample 12. A probe source 230 generates a probe beam 232 which is reflected off the sample. A detector 234 is provided to monitor the power of the specularly reflected beam. To the extent that the thermal waves modulate the optical reflectivity of the sample, a modulated output will be generated by the detector. As in the previous embodiments, the output of the detector is supplied to the processor, along with the output from modulator to allow phase synchronous detection.

Figure 9:
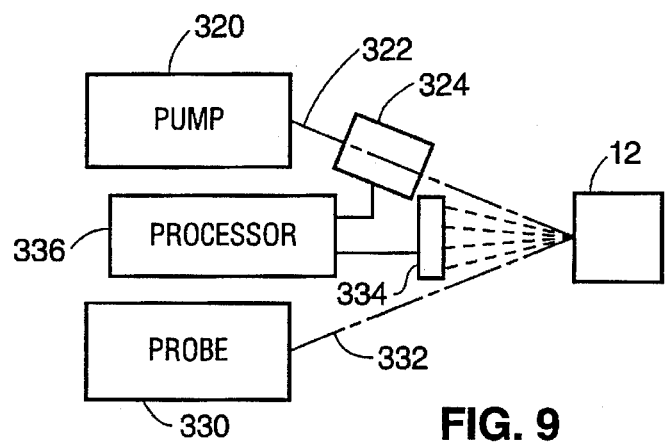
FIG. 9 is a schematic diagram of a thermal wave detection system for monitoring the modulated optical scattering of a probe beam.

FIG. 9 is a schematic diagram of a thermal wave detection system that relies on the measurement of the scattering of the probe beam. A pump source 320 generates a pump beam 322 which is passed through a modulator 324 to periodically heat selected constituents in the sample 12. A probe source 330 generates a probe beam 322 which is directed to the sample as well. Detector 334 is positioned in a manner to measure non-specularly reflected light from the probe beam which has been scattered after interaction with the sample.

To the extent the sample is periodically heated, periodic changes in the complex index of refraction and possibly deformations at the sample surface will occur in response to the thermal waves in the sample. These effects will modulate the optical scattering of the probe beam. This principal is discussed in greater detail in U.S. Pat. No. 4,632,561. The output of the detector 334 is supplied to a processor 336. In the manner described above, the sample can be analyzed through a phase synchronous detection scheme.

Figure 10:
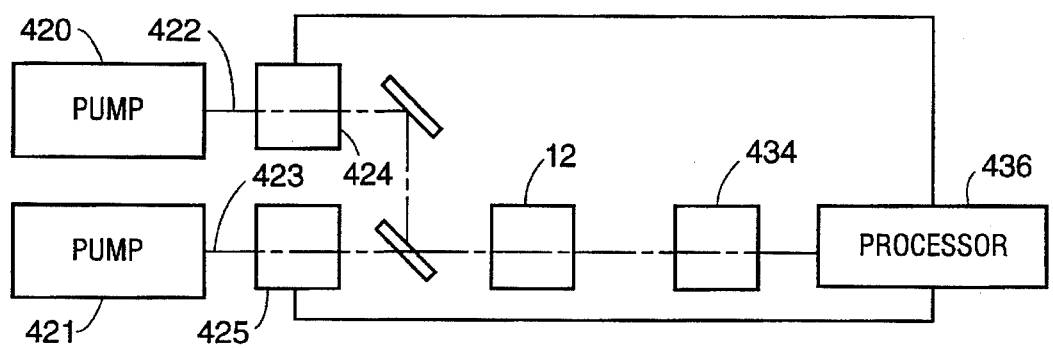
FIG. 10 is a schematic diagram of a thermal wave detection system utilizing a double modulated pump and probe beam combination.

FIG. 10 shows an alternate approach wherein the functions of the pump and probe beams are combined. In this system, two pump sources 420 and 421 are provided for generating beams 422 and 423. Each of the pump beams is passed through a separate modulator 424 and 425 for imposing two distinct modulation frequencies $\omega_1$ and $\omega_2$. These two beams are then combined with appropriate optics and passed through the sample 12 to periodically heat selected constituents therein. The modulated transmitted (or reflected) power of the combined beams is measured by detector 434. The modulated transmittance (or reflectance) signals will be present at both the two pump frequencies $\omega_1$ and $\omega_2$, as well as the cross products $(\omega_1+\omega_2)$ and $(\omega_1-\omega_2)$. Preferably, the phase synchronous detection is carried out at the difference frequency which will be lower than and different from either of the two pump frequencies. Further details relating to this type of dual frequency pumping process can be found in U.S. Pat. Nos. 5,206,710 and 5,408,327.

Figure 11:
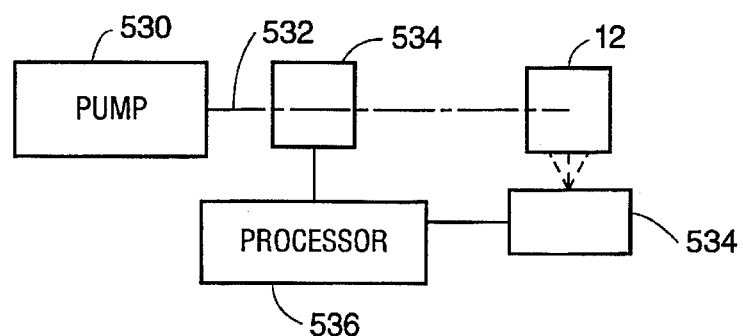
FIG. 11 is a schematic diagram of a thermal wave detection system wherein the thermal wave effects are monitored with non-optical detection devices.

All of the embodiments discussed so far have included a means for optically monitoring the thermal wave response in the sample. Other approaches for monitoring the thermal wave response can also be used. FIG. 11 illustrates a generic schematic diagram for such a system. As in the previously described systems, a pump source 530 is provided for generating a pump beam 532. The pump beam is passed through a modulator 534 and then directed to the sample to periodically heat selected constituents therein. The periodic heating will affect a number of parameters in the sample which could be measured by various detectors 534. For example, detector 534 could consist of an ultrasonic imager for transmitting acoustic waves into the sample. In an ultrasonic imager, the reflected or scattered acoustic waves are measured to provide information about the sample. In accordance with the subject invention, the ultrasound response that occurs at the periodic excitation frequency can be extracted to isolate the thermal wave effects. It would also be possible to use detector systems based on microwaves or magnetic resonance imaging. In all cases, the modulated response should be determined. In addition, in order to analyze constituents of interest which are separate from the constituents that have been periodically heated, it would be desirable to select an appropriate modulation frequency and to isolate the π/2 phase signal.

In the illustrated embodiments, an intensity modulated optical light beam has been used to induce periodic heating in the sample. Other possible mechanisms for providing the preferential periodic heating to selected constituents in the sample would include microwaves, focused ultrasound or X-rays.

While the subject invention has been described with reference to the preferred embodiments, various changes and modifications could be made therein, by one skilled in the art, without varying from the scope and spirit of the subject invention as defined by the appended claims.

I claim:

1. An apparatus for analyzing properties of a sample, said sample being non-homogeneous and including at least first and second constituents, said apparatus comprising:

means for selectively inducing a periodic heating at a predetermined frequency in said first constituents in the sample in a manner to create thermal waves therein and wherein said predetermined frequency is selected to substantially confine the thermal waves to the first constituents when the properties of said first constituent are to be analyzed, and wherein the predetermined frequency is selected so that the thermal waves will spread out to reach the second constituents when the properties of the second constituents are to be analyzed;

a phase synchronous detector for monitoring periodic effects of the thermal waves on the sample and generating an output signal, and wherein the portion of the output signal which is in phase with respect to the periodic heating will be primarily from the first constituents while the portion of the output signal which is ninety degrees out of phase with the periodic heating will be primarily from the second constituents when the predetermined frequency has been selected so that the thermal waves spread out to reach the second constituents; and processor means for analyzing the sample based on the output signal generated by said detector and with the frequency of the periodic heating and the phase of the output signal of the detector with respect to the periodic heating being selected to target the analysis to one of the first or second constituents in the sample.

2. An apparatus as recited in claim 1 wherein the frequency of the periodic heating is selected so that the spread of the thermal waves is primarily confined to the first constituents.

3. An apparatus as recited in claim 1 wherein the detector is configured to monitor periodic effects of the thermal waves which are in-phase with the periodic heating.

4. An apparatus as recited in claim 3 wherein the detector is configured to also monitor periodic effects of the thermal waves which are approximately ninety degrees out of phase with the periodic heating and wherein the out-of-phase signals are used to normalize the in-phase signals.

5. An apparatus as recited in claim 1 wherein the frequency of the periodic heating means is selected so that the thermal waves will spread and interact with the second constituents.

6. An apparatus as recited in claim 5 wherein the detector is configured to monitor periodic effects of the thermal waves which are approximately ninety degrees out of phase with the periodic heating permitting targeting of the second constituent.

7. An apparatus as recited in claim 6 wherein the frequency of the periodic heating means is selected so that the thermal diffusion length of the thermal waves will be equal to approximately half an average distance between the first constituents.

8. An apparatus as recited in claim 6 wherein the frequency of the periodic heating means is selected so that the thermal diffusion length of the thermal waves will be equal to approximately $(2/\pi)$ times the average distance between the first and second constituents.

9. An apparatus as recited in claim 1 wherein said periodic heating means includes:

a light source for generating a pump beam having a wavelength which is preferentially absorbed in said first constituents of said sample;

means for intensity modulating said pump beam at a predetermined frequency; and means for directing the pump beam to the sample so that the energy of the pump beam is absorbed in said first constituents in a manner to generate thermal waves emanating therefrom.

10. An apparatus as recited in claim 1 wherein said detector includes an ultrasonic imager.

11. An apparatus as recited in claim 1 wherein said detector includes a microwave generator and detector.

12. An apparatus as recited in claim 1 wherein said detector includes a magnetic resonance imager.

13. An apparatus as recited in claim 1 wherein said detector includes a light source for generating a probe beam and a means for directing the probe beam to interact with the sample.

14. An apparatus as recited in claim 13 wherein the wavelength of the probe beam is selected to be preferentially absorbed in the targeted constituent.

15. An apparatus as recited in claim 13 wherein the detector functions to measure modulated changes in power of the probe beam after it has interacted with the sample.

16. An apparatus as recited in claim 13 wherein the detector functions to measure modulated changes in reflected power of the probe beam.

17. An apparatus as recited in claim 13 wherein the detector functions to measure modulated changes in transmitted power of the probe beam.

18. An apparatus as recited in claim 13 wherein the detector functions to measure modulated changes in scattering of the probe beam.

19. An apparatus as recited in claim 13 wherein the detector functions to measure modulated changes in a polarization state of the probe beam.

20. An apparatus for a non-invasive, in vivo analysis of constituents carried in blood of a living mammal, said blood including red blood cells having hemoglobin therein, said apparatus comprising:

a first light source for generating a pump beam having a wavelength which is preferentially absorbed in the hemoglobin of red blood cells;

means for intensity modulating said pump beam at a predetermined frequency;

means for directing the pump beam through a skin of the mammal and into the blood so that the energy of the pump beam is absorbed in the red blood cells in a manner to generate thermal waves emanating therefrom;

a second light source for generating a probe beam;

means for directing the probe beam through the skin of the animal and into the blood;

a phase synchronous detector for monitoring the periodic changes in the probe beam caused by the thermal waves in the blood and generating an output signal; and processor means for analyzing the constituents in the blood based on the output signal generated by said detector and with the modulation frequency of the pump beam and the phase of the output signal of the detector with respect to the periodic heating being selected to target the analysis to selected constituents in the sample.

21. An apparatus as recited in claim 20 wherein the frequency of the periodic heating is selected so that the spread of the thermal waves is primarily confined to the red blood cells.

22. An apparatus as recited in claim 20 wherein the detector is configured to monitor periodic effects of the thermal waves which are in-phase with the periodic heating.

23. An apparatus as recited in claim 22 wherein the detector is configured to also monitor periodic effects of the thermal waves which are approximately ninety degrees out of phase with the periodic heating and wherein the out-of-phase signals are used to normalize the in-phase signals.

24. An apparatus as recited in claim 20 wherein the frequency of the periodic heating means is selected so that the thermal waves will spread beyond the hemoglobin to other constituents in the blood.

25. An apparatus as recited in claim 24 wherein the detector is configured to monitor periodic effects of the thermal waves which are approximately ninety degrees out of phase with the periodic heating permitting targeting of the other constituents in the blood.

26. An apparatus as recited in claim 25 wherein the frequency of the periodic heating means is selected so that the thermal diffusion length of the thermal waves will be equal to approximately half an average distance between the red blood cells.

27. An apparatus as recited in claim 20 wherein the wavelength of the probe beam is selected to be preferentially absorbed in the targeted constituent.

28. An apparatus as recited in claim 20 wherein the detector functions to measure modulated changes in power of the probe beam after it has interacted with the sample.

29. An apparatus as recited in claim 28 wherein the detector functions to measure modulated changes in reflected power of the probe beam.

30. An apparatus as recited in claim 28 wherein the detector functions to measure modulated changes in transmitted power of the probe beam.

31. An apparatus as recited in claim 20 wherein the detector functions to measure modulated changes in scattering of the probe beam.

32. An apparatus as recited in claim 20 wherein the detector functions to measure modulated changes in a polarization state of the probe beam.

33. An apparatus as recited in claim 20 wherein the targeted constituent is glucose and wherein said probe beam is linearly polarized prior to interacting with the glucose and wherein said detector monitors the modulated polarization rotation of the beam.

34. An apparatus as recited in claim 33 wherein the wavelength of the probe beam is selected to be in the visible region.

35. An apparatus as recited in claim 20 wherein the targeted constituent is glucose and wherein said probe beam is alternately left and right-hand circularly polarized prior to interacting with the blood stream and wherein said detector monitors a modulated ratio of transmitted left and right-hand circular polarized light of the probe beam.

36. An apparatus as recited in claim 35 wherein the wavelength of the probe beam is selected to be in a near infrared range.

37. An apparatus for non-invasive, in vivo analysis of glucose carried in a blood stream of a living mammal, said blood stream also carrying red blood cells having hemoglobin therein, said apparatus comprising:

a first light source for generating a pump beam having a wavelength which is preferentially absorbed in the hemoglobin of red blood cells;

means for intensity modulating said pump beam at a predetermined frequency;

means for directing the pump beam through a skin of the mammal and into the blood stream so that the energy of the pump beam is absorbed in the red blood cells in a manner to generate thermal waves emanating therefrom, with the modulation frequency of the pump beam being selected so that the thermal waves extend beyond the hemoglobin and interact with the glucose in the blood stream;

a second light source for generating a probe beam;

means for directing the probe beam through the skin of the mammal and into the blood stream;

a phase synchronous detector for monitoring periodic changes in the probe beam caused by the thermal waves interacting with the glucose in the blood stream and generating an output signal responsive thereto, said detector for monitoring the periodic changes in the probe beam that are approximately ninety degrees out of phase with respect to the thermal waves; and processor means for analyzing a concentration of glucose in the blood stream based on the output signal generated by said detector.

38. An apparatus as recited in claim 37 wherein the modulation frequency of the pump beam is selected so that the thermal diffusion length of the thermal waves will be equal to approximately half the average distance between red blood cells.

39. An apparatus as recited in claim 37 wherein said probe beam is linearly polarized prior to interacting with the glucose and wherein said detector monitors modulated changes in a polarization rotation of the beam.

40. An apparatus as recited in claim 39 wherein the wavelength of the probe beam is selected to be in the visible range.

41. An apparatus as recited in claim 39 wherein said probe beam is alternately left and right-hand circularly polarized prior to interacting with the blood stream and wherein said detector monitors a modulated ratio of the transmitted left and right-hand circular polarized light of the probe beam.

42. An apparatus as recited in claim 41 wherein the wavelength of the probe beam is selected to be in a near infrared range.

43. An apparatus as recited in claim 37 wherein the wavelength of the pump beam is between 400 and 600 nm.

44. An apparatus as recited in claim 37 wherein the modulation frequency of the pump beam is on an order of 10 kHz.

45. An apparatus as recited in claim 37 wherein the detector functions to measure modulated changes in transmitted power of the probe beam.

46. An apparatus as recited in claim 45 wherein the wavelength of the probe beam is selected to be in the visible range.

47. A method for analyzing properties of a sample, said sample being non-homogenous and including at least first and second constituents, said method comprising the steps of:
generating a pump beam having a wavelength which is preferentially absorbed in the first constituents, said pump beam being intensity modulated with a predetermined frequency;
directing the pump beam to interact with the sample to selectively induce a periodic heating in the first constituents in a manner to generate thermal waves emanating therefrom, and wherein the modulation frequency of the pump beam is selected so that the thermal waves extend beyond the first constituents and interact with the second constituents;
generating a probe beam;
directing the probe beam to interact with the sample;
monitoring periodic changes in the probe beam caused by the thermal waves interacting with the second constituents and generating an output signal responsive thereto, and with the monitored periodic changes being approximately ninety degrees out of phase with the periodicity of the thermal waves; and
analyzing the second constituents in the sample based on the output signal.

48. A method as recited in claim 47 wherein the modulation frequency of the pump beam is selected so that the thermal diffusion length of the thermal waves will be equal to approximately half the average distance between the first constituents.

49. A method as recited in claim 47 wherein the modulation frequency of the pump beam is selected so that the thermal diffusion length of the thermal waves will be equal to approximately $(2/\pi)$ times the average distance between the first and second constituents.

50. A method as recited in claim 47 wherein modulated changes in power of the probe beam are monitored after it has interacted with the sample.

51. A method as recited in claim 47 wherein modulated changes in reflected power of the probe beam are monitored.

52. A method as recited in claim 47 wherein modulated changes in transmitted power of the probe beam are monitored.

53. A method as recited in claim 47 wherein modulated changes in scattering of the probe beam are monitored.

54. A method as recited in claim 47 wherein modulated changes in a polarization state of the probe beam are monitored.

55. A method as recited in claim 47 wherein the sample is blood and the first constituent is hemoglobin and the second constituent is glucose and wherein said probe beam is linearly polarized prior to interacting with the glucose and wherein the modulated polarization rotation of the beam is monitored.

56. A method as recited in claim 47 wherein the sample is blood and the first constituent is hemoglobin and the second constituent is glucose and wherein said probe beam is alternately left and right-hand circularly polarized prior to interacting with the blood stream and wherein a modulated ratio of the transmitted left and right-hand circular polarized light of the probe beam is monitored.

57. A method for a non-invasive, in vivo analysis of glucose carried in a blood stream of a living mammal, said blood stream also carrying red blood cells having hemoglobin therein, said method comprising the steps of:
generating a pump beam having a wavelength which is preferentially absorbed in the hemoglobin of red blood cells;
intensity modulating said pump beam at a predetermined frequency;
directing the pump beam through a skin of the mammal and into the blood stream so that the energy of the pump beam is absorbed in the red blood cells in a manner to generate thermal waves emanating therefrom, with the modulation frequency of the pump beam being selected so that the thermal waves extend beyond the hemoglobin and interact with the glucose in the blood stream;
generating a probe beam;
directing the probe beam through the skin of the mammal and into the blood stream;
monitoring periodic changes in the probe beam caused by the thermal waves interacting with the glucose in the blood stream and generating an output signal responsive thereto, and with the monitored periodic changes in the probe beam being approximately ninety degrees out of phase with the periodicity of the thermal waves; and
analyzing a concentration of glucose in the blood stream based on the output signal generated by said detector.

58. A method as recited in claim 57 wherein the modulation frequency of the pump beam is selected so that the thermal diffusion length of the thermal waves will be equal to approximately half the average distance between red blood cells.

59. A method as recited in claim 57 wherein the probe beam is linearly polarized prior to interacting with the glucose and wherein modulated changes in polarization rotation of the beam are monitored.

60. A method as recited in claim 59 wherein the wavelength of the probe beam is selected to be in a visible region.

61. A method as recited in claim 57 wherein said probe beam is alternately left and right-hand circularly polarized prior to interacting with the blood stream and wherein a modulated ratio of the transmitted left and right-hand circular polarized light is monitored.

62. A method as recited in claim 61 wherein the wavelength of the probe beam is selected to be in a near infrared range.

63. A method as recited in claim 57 wherein the wavelength of the pump beam is between 400 and 600 nm.

64. A method as recited in claim 57 wherein the modulation frequency of the pump beam is on an order of 10 kHz.

65. A method as recited in claim 57 wherein modulated changes in transmitted power of the probe beam are monitored.

66. A method as recited in claim 65 wherein the wavelength of the probe beam is selected to be in a visible range.

67. An apparatus for analyzing properties of a sample, said sample being non-homogenous and including at least first and second constituents, said apparatus comprising:
a first light source for generating a pump beam having a wavelength which is preferentially absorbed in the first constituents, said pump beam being intensity modulated with a predetermined frequency;

means for directing the pump beam to interact with the sample to selectively induce a periodic heating in the first constituents in a manner to generate thermal waves emanating therefrom, and wherein the modulation frequency of the pump beam is selected so that the thermal waves extend beyond the first constituents and interact with the second constituents;

a second light source for generating a probe beam;

means for directing the probe beam to interact with the sample;

a phase synchronous detector for monitoring periodic changes in the probe beam caused by the thermal waves interacting with the second constituents and generating an output signal responsive thereto, and with the monitored periodic changes being approximately ninety degrees out of phase with respect to the thermal waves; and a processor for analyzing the second constituents in the sample based on the output signal from the detector.

68. An apparatus as recited in claim 67 wherein modulated changes in transmitted power of the probe beam are monitored.

69. An apparatus as recited in claim 67 wherein modulated changes in the polarization state of the beam are monitored.

70. An apparatus as recited in claim 67 wherein said probe beam is alternately left and right-hand circularly polarized prior to interacting with the sample and wherein said detector monitors a modulated ratio of the transmitted left and right-hand circular polarized light of the probe beam.

71. A method for analyzing properties of a sample, said sample being non-homogeneous and including at least first and second constituents, said apparatus comprising:

selectively inducing a periodic heating at a predetermined frequency in said first constituents in the sample in a manner to create thermal waves therein and wherein said predetermined frequency is selected to substantially confine the thermal waves to the first constituents when the properties of said first constituent are to be analyzed, and wherein the predetermined frequency is selected so that the thermal waves will spread out to reach the second constituents when the properties of the second constituents are to be analyzed;

monitoring periodic effects of the thermal waves on the sample and generating an output signal, and wherein the portion of the output signal which is in phase with respect to the periodic heating will be primarily from the first constituents while the portion of the output signal which is ninety degrees out of phase with the periodic heating will be primarily from the second constituents when the predetermined frequency has been selected so that the thermal waves spread out to reach the second constituents; and analyzing the sample based on the output signal and with the frequency of the periodic heating and the phase of the output signal with respect to the periodic heating being selected to target the analysis to one of the first or second constituents in the sample.

72. A method as recited in claim 71 wherein the frequency of the periodic heating is selected so that the spread of the thermal waves is primarily confined to the first constituents.

73. A method as recited in claim 71 wherein periodic effects of the thermal waves which are in-phase with the periodic heating are monitored.

74. A method as recited in claim 73 wherein periodic effects of the thermal waves which are approximately ninety degrees out of phase with the periodic heating are monitored and wherein the out-of-phase signals are used to normalize the in-phase signals.

75. A method as recited in claim 71 wherein the frequency of the periodic heating is selected so that the thermal waves will spread and interact with the second constituents.

76. A method as recited in claim 75 wherein the periodic effects of the thermal waves which are approximately ninety degrees out of phase with the periodic heating are monitored permitting targeting of the second constituent.

77. A method as recited in claim 76 wherein the frequency of the periodic heating is selected so that the thermal diffusion length of the thermal waves will be equal to approximately half an average distance between the first constituents.

78. A method as recited in claim 76 wherein the frequency of the periodic heating is selected so that the thermal diffusion length of the thermal waves will be equal to approximately $(2/\pi)$ times an average distance between the first and second constituents.

* * * * *